United States Patent

Durand et al.

Patent Number: 5,853,757
Date of Patent: Dec. 29, 1998

[54] CARRIER FOR ANIMAL MEDICATION

[76] Inventors: Mark Roger Durand; Debra Marie Durand, both of 13572 49th St., N., Royal Palm Beach, Fla. 33411

[21] Appl. No.: 854,499

[22] Filed: May 12, 1997

[51] Int. Cl.$^6$ ........................................ A61K 9/48
[52] U.S. Cl. .................... 424/451; 424/439; 424/442; 424/452; 424/456; 424/464
[58] Field of Search ................... 424/451, 456, 424/439, 452, 442, 464

[56] References Cited

U.S. PATENT DOCUMENTS

| | | | |
|---|---|---|---|
| 3,789,845 | 2/1974 | Long | 128/264 |
| 4,905,867 | 3/1990 | Claassen | 221/30 |
| 5,296,209 | 3/1994 | Simone et al. | 424/49 |
| 5,399,162 | 3/1995 | Cselle | 604/60 |
| 5,674,515 | 10/1997 | Wesenhagen | 424/405 |

*Primary Examiner*—Thurman K. Page
*Assistant Examiner*—Kathryne E. Shelborne
*Attorney, Agent, or Firm*—McHale & Slavin, PA

[57] ABSTRACT

A carrier for pills, tablets, or capsules allowing for ease of oral consumption by animals. The carrier having a preformed chamber allowing for the insertion of medication therein, the carrier is deformable causes securement of the medication within the chamber. The carrier masks the scent of medication and including a lubricant to allow for ease of consumption of the carrier and contained medication.

9 Claims, 1 Drawing Sheet

CARRIER FOR ANIMAL MEDICATION

FIELD OF THE INVENTION

This invention relates generally to the medication of animals and, more specifically, to a preformed carrier for pills, tablets, or capsules having a chamber for insertion thereof, said carrier masking the scent of medication and including a lubricant to allow for ease of consumption.

BACKGROUND OF THE INVENTION

Pet owners share a common problem in the dispensing of medication to their pets. This is a particular problem with dogs for a dog is capable of detecting a scent over one hundred times greater than a human. The dog is able to detect medication which is found offensive to most pets. For this reason, it is difficult to cause the animal to swallow the medication.

With small dogs, a pill or tablet may be large enough that the animal must first chew the medication in order to swallow it. This may be performed by breaking up the medication, which can release a strong medicine scent. Alternatively the medication may be forced down the dog's throat. In larger dogs, there is a risk that the physical insertion of such medication into the dog's throat may result in a dog bite.

For these reasons, various types of medicine applications have been attempted, some of which work well for some dogs yet fail with others. For example, it may be possible to mix the medication within food wherein the medication is consumed as a treat. However, dog foods are natural foods that cannot mask the scent of normal medication. Typically the sprinkling of the medication on the dog food may cause the dog to reject eating, leading to further problems.

Yet another method of inserting medication is the use of a piece of meat wherein the medication is pressed into the food and the food delivered to the animal in the form of a dog treat. In most instances, this application also fails as the owner handles the medication during the insertion process which in turn covers the outer surface of the food with the scent. In addition, the meat must be of the correct substance for if it is too dry, it will fall apart or cause the animal to choke. If the meat is too moist, it will be difficult to work with and will not hold the medication. Further, high moisture will cause the medication to dissolve which may cause the release of the medication scent. If the scent is released, the dog will again be able to detect the scent of the medication either through the direct access or through the handling of the food.

Various devices have been patented so as to assist in this pill dispensing process, the obvious discomfort to a small animal is readily apparent. U.S. Pat. No. 5,584,805 discloses a pill-dispensing gun made from PVC pipe having a core with a rigid tube which extends through the tube and then couples to a plunger. The PVC pipe is inserted down the animal's throat when a plunger injects the pills into the animal's throat in such a position so as to force swallowing of the pill.

U.S. Pat. No. 5,399,162 discloses a device that also is used for insertion of medication down the throat of the animal. A spring biased rod is used for injecting the medication down the animal's throat.

U.S. Pat. No. 3,789,845 discloses a syringe type holder used for administrating the capsules or tablets to the animals. This device uses a sticky food material to adhere a tablet to a plug which is then inserted down the animal's throat. When it is far enough, the syringe pressure is released allowing release of medication.

Thus, what is lacking in the art is a structure that allows for the inexpensive administration of medicine, said structure capable of masking the medication scent and includes a lubricant to assist the animal in swallowing.

SUMMARY OF THE INVENTION

The present invention consists of a digestible carrier and composition therefor that allows for ease of delivering a tablet, capsule, pill with like medication to an animal. The carrier is formed from a material that is found most favorable by animals and forms such a chamber structure for securing medication.

The chamber is available for receipt of medication which is sealed into the chamber upon the deformation of the carrier. Actual use allows and individual to insert the medication within the chamber with one hand and close the chamber with the second hand so as not to taint the outer surface of the carrier with the scent of the medication. The carrier masks the scent of the medication should the animal sniff the carrier before placing in its mouth. The carrier can than be swallowed whole, wherein a lubricant assists such an act, or chewed wherein the carrier material of construction is formed by meat by-products found favorable to most animals.

In the preferred embodiment, the carrier is formed from a composition of soy flour, glycerin, and various meat by-products. The composition is dehydrated which allows the carrier to maintain a preformed shape having an opening leading to a chamber. The carrier maintains a level of moisture which facilitates closure for sealing the medication in the chamber. The glycerine acts as a lubricant to assist the animal in swallowing of the carrier and associated medication. The glycerin reacts with the saliva to prevent the animal from choking on the hard medicine.

Thus, an objective of the instant invention is to provide a simple and inexpensive carrier for delivery of medicine to animals without the need for insertion of objects into the animal's throat.

Another object of the instant invention is to set forth a device for use in administering medicine that conceals the scent of the medication and minimizes handling by the human.

Yet still another object of the instant invention is to set forth a preformed chamber which allows for the insertion of various types of oral medication so as to seal the medication within a preformed chamber to prohibit the animal from smelling of the medication before the medication is placed into the animal's mouth.

Still yet another object of the instant invention is to provide a carrier for medicine which allows the animal to consume the medication with a passive positioning of the medication to inspire relaxation and calmness.

Yet still another object of the instant invention is to provide a carrier that operates as for concealment of liquid or solid medications.

Yet another object of the instant invention is to provide a carrier that is firm enough to maintain a shaped chamber yet includes a lubricant to assist the animal in chewing and swallowing of the carrier.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 1:
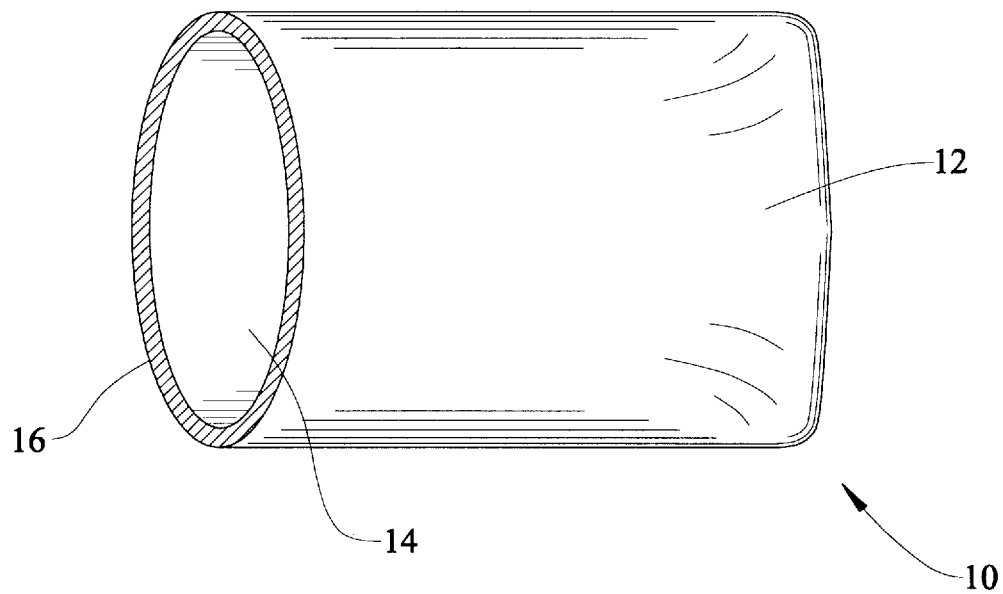
FIG. 1 is a perspective view in a large scale of the animal medication carrier illustrating an opening allowing insertion of medication into the carrier.

Referring to FIG. 1, set forth is the carrier 10 of the instant invention for use with animal medication. The carrier is formed from soft edible material 12 creating a sack-like structure with an interior chamber 14 accessible by a neck opening 16. The carrier 10 includes dehydrated meat by-products admixed with a soy flour and a fluid lubricant. The carrier is approximately 66% meat by-product; approximately 17% soy flour; approximately 5% water; and approximately 7% glycerine with the remainder of the materials being inert. The by-products are preferably a mixture of beef and liver. The soy flour is considered the binding agent, however, it is noted that other binding agents can be used and are deemed within the scope of this invention. A food coloring may be added to enhance the appearance of the carrier. For instance, a red color number 40 and number 3 may be used to enhance the appearance of the carrier so as to resemble fresh meat.

The soy flour maintains the carrier in a soft pliable state when use with a water soluble glycerine which operates as a lubricant. Should an animal swallow the carrier whole, the glycerine reacts with the saliva causing a slick surface allowing the carrier to swallowed without discomfort to the animal. The meat by-products are used for masking the scent of the medicine should the animal sniff the carrier before placing in its mouth. Should the animal chew the carrier, the meat continues to mask the medicine taste and the glycerine allows the carrier to become soft almost immediately causing the animal to swallow.

Formation of the carrier requires the meat by-products to be cooked, preferably at approximately 300 degrees fahrenheit for 30 minutes and then strained. The meat is then ground through a processor into a fine structureless composition. Soy flour, glycerine, and a small amount of water is then added to the composition until a dough-like consistency allows the materials to be formed into the sack-like shape by use of a mold. The carrier is then dehydrated for approximately ½ hour, cooled and then placed into an airtight container. Once dehydrated carrier retaining the sack-like shape.

Stored in an airtight container prevents the loss of textured consistency until use. More importantly, the meat by-products lack preservatives thereby requiring the airtight container and refrigeration once the container has been opened. A preservative can be added, however, it has been found that an animal on medication may have an allergic reaction to various preservatives and care must be taken that the preservative chosen does not react with the medication.

Upon use, an individual holds the carrier in one hand and inserts a pill, tablet, capsule, or liquid medication into the chamber. The neck opening allows for ease of insertion eliminating the need for having the hand touching the medication also touch the outside of the carrier. Once the medication has been inserted, the individual squeezes the carrier shut to seal the medication within the chamber. By use of one hand hold the carrier, the opposite hand can be used to insert the medication. The carrier is then closed by the hand used to hold the carrier to avoid placing the scent on the outside of the carrier. The carrier can then be placed into the mouth of the animal wherein the animal will either swallow the carrier whole, or chew the carrier wherein the meat by-product masks the flavor of the medicine.

Figure 2:
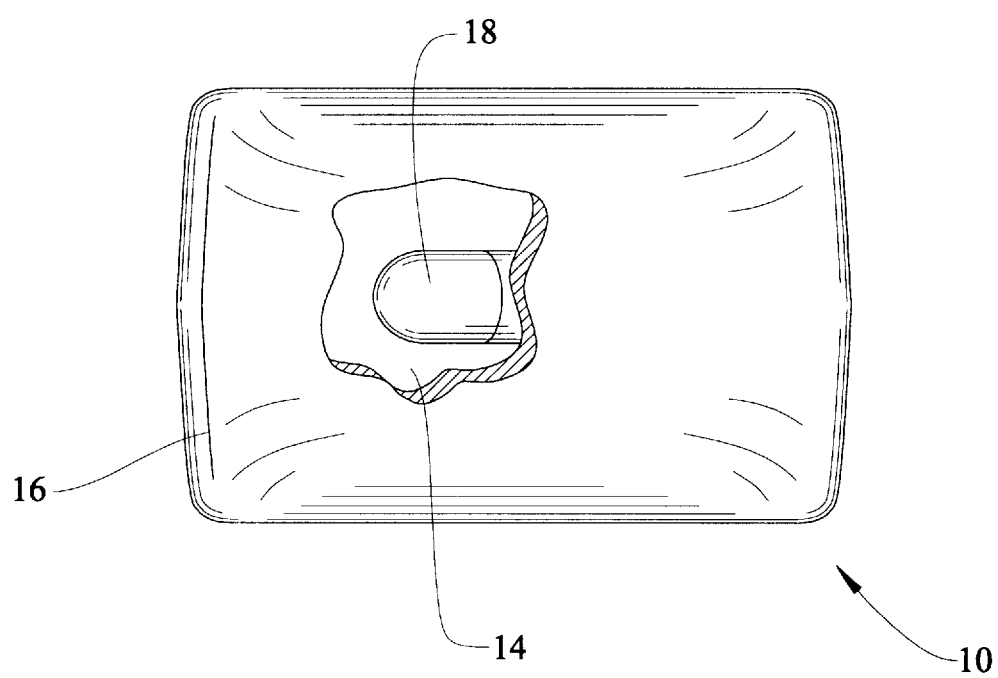
FIG. 2 is a perspective view of the animal medication carrier of the instant invention in a sealed position with a cut-away view illustrating an internal chamber with a medication tablet secured therein.

As shown in FIG. 2, the carrier 10 has the neck opening 16 illustrate in a closed position. Tablet 18 is secured within the chamber 14 thereby concealing the medication from the animal. The preferred lubricant for use with the carrier is glycerine which does not evaporate easily and reacts with water so as to form a slick surface thereby assisting in swallowing of the carrier with the dog's saliva.

In a breakdown of a single carrier, the preferred embodiment would include 1.66 grams of beef, 4.16 grams of liver by-product, 0.83 grams of beef fat by-product, 1.66 grams of soy flour, 0.5 grams of water, 0.66 grams of glycerin, and 0.08 grams of a color dye.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

What is claimed is:

1. In the method of having an animal swallow a pill, tablet or capsule, the improvement comprising:

forming a soft edible sack from a dehydrated meat by-product admixed with a soy flour and water mixture and a glycerine lubricant adapted to react with the animal's saliva thereby providing a slick surface to facilitate swallowing thereof, said sack having an interior chamber with a neck opening leading to said chamber;

inserting a pill, tablet or capsule into said chamber of said sack;

sealing said chamber by deforming of said neck opening;

placing said sack in the mouth of an animal.

2. The method according to claim 1 wherein said sack is formed from:

cooking by-products from the meat group of beef and liver;

straining said cooked meat by-products;

grinding said by-products until fine;

admixing said ground by-products with soy flour and glycerine into a uniform mixture;

placing said mixture into a mold and forming a sack with a chamber in said sack;

dehydrating said sack and placing said sack into an airtight container until use.

3. The method according to claim 2 wherein said sack is approximately 66 percent meat by-product; approximately 17 percent soy flour; approximately 5 percent water; approximately 7 percent glycerin, and the remainder of inert material.

4. The method according to claim 2 wherein said sack includes a food coloring.

5. A carrier for animal medication comprising:

a sack constructed from a soft edible material forming an interior chamber with a neck opening leading to said chamber;

a glycerin lubricant admixed in said material;

wherein said chamber is available for receipt of medicine and said neck opening is sealable in a closed position for securing the medicine in said chamber.

6. The carrier for animal medication according to claim 5 wherein said sack is a dehydrated meat by-product admixed with a soy flour and a liquid.

7. In the method of having an animal swallow a pill, tablet or capsule, the improvement comprising:

forming a soft edible sack from a dehydrated meat by-product admixed with a soy flour and a fluid lubricant, said sack having an interior chamber with a neck opening leading to said chamber;

inserting a pill, tablet or capsule into said chamber of said sack;

sealing said chamber by deforming of said neck opening;

placing said sack in the mouth of an animal, and wherein said sack is formed from;

cooking by-products from the meat group of beef and liver;

straining said cooked meat by-products;

grinding said by-products until fine;

admixing said ground by-products with soy flour and glycerine into a uniform mixture;

placing said mixture into a mold and forming a sack with a chamber in said sack; and dehydrating said sack and placing said sack into an airtight container until use.

8. The method according to claim 7 wherein said sack is approximately 66 percent meat by-product; approximately 17 percent soy flour; approximately 5 percent water; approximately 7 percent glycerin, and the remainder of inert material.

9. The method according to claim 7 wherein said sack includes a food coloring.

* * * * *